(12) United States Patent
Marshall

(10) Patent No.: US 11,879,020 B2
(45) Date of Patent: Jan. 23, 2024

(54) CYCLIC PEPTIDOMIMETIC FOR THE TREATMENT OF NEUROLOGICAL DISORDERS

(71) Applicant: Brown University, Providence, RI (US)

(72) Inventor: John Marshall, Barrington, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 17/690,809

(22) Filed: Mar. 9, 2022

(65) Prior Publication Data

US 2022/0194986 A1 Jun. 23, 2022

Related U.S. Application Data

(63) Continuation of application No. 17/036,059, filed on Sep. 29, 2020, now abandoned.

(60) Provisional application No. 62/909,396, filed on Oct. 2, 2019.

(51) Int. Cl.
| | | |
|---|---|---|
| *C07K 7/52* | (2006.01) | |
| *A61P 25/28* | (2006.01) | |
| *A61P 9/10* | (2006.01) | |
| *A61P 25/22* | (2006.01) | |
| *A61P 25/24* | (2006.01) | |

(52) U.S. Cl.
CPC ............. *C07K 7/52* (2013.01); *A61P 9/10* (2018.01); *A61P 25/22* (2018.01); *A61P 25/24* (2018.01); *A61P 25/28* (2018.01)

(58) Field of Classification Search
CPC ..... C07K 7/52; C07K 7/56; A61P 9/10; A61P 25/22; A61P 25/24; A61P 25/28
See application file for complete search history.

(56) References Cited

U.S. PATENT DOCUMENTS

| | | | |
|---|---|---|---|
| 8,673,857 | B2 | 3/2014 | Marshall et al. |
| 9,403,876 | B2 | 8/2016 | Spaller et al. |
| 2012/0149646 | A1* | 6/2012 | Marshall ............... A61P 25/00 514/17.7 |
| 2012/0220535 | A1 | 8/2012 | Spaller et al. |
| 2015/0038671 | A1 | 2/2015 | Parang et al. |
| 2015/0126457 | A1 | 5/2015 | Goebel et al. |
| 2017/0107253 | A1 | 4/2017 | Goebel et al. |
| 2018/0228421 | A1 | 8/2018 | Saab |

OTHER PUBLICATIONS

Kuhn et al (Neuropsychopharmacology, 2016, 41, 1521-1529) (Year: 2016).*
Vignaud et al (Frontiers in Human Neuroscience, Feb. 2019, vol. 13, article 72, 1-8) (Year: 2019).*
Cao et al., "Impairment of TrkB-PSD-95 Signaling in Angelman Syndrome", PLOS Biology, vol. 11, Issue 2, e1001478, Feb. 2013, 17 pages.
Koike et al., "Effects of Ketamine and LY341495 on the Depressive-Like Behavior of Repeated Corticosterone-Injected Rats", Pharmacology, Biochemistry and Behavior, vol. 107, Jun. 2013, pp. 20-23.
Marshall et al., "Antidepression Action of BDNF Requires and is Mimicked by Gαi1/3 Expression in the Hippocampus", Proceedings of the National Academy of Sciences, vol. 115, No. 15, 2018, pp. E3549-E3558.
Marshall et al., "Inhibition of N-Methyl-D-aspartate-induced Retinal Neuronal Death by Polyarginine Peptides Is Linked to the Attenuation of Stress-induced Hyperpolarization of the Inner Mitochondrial Membrane Potential", The Journal of Biological Chemistry, vol. 290, No. 36, Sep. 4, 2015, pp. 22030-22048.
Najjar, et al., "An L-to D-Amino Acid Conversion in an Endosomolytic Analog of the Cell-Penetrating Peptide TAT Influences Proteolytic Stability, Endocytic Uptake, and Endosomal Escape", The Journal of Biological Chemistry, vol. 292, No. 3, Jan. 20, 2017, pp. 847-861.
Purkayastha, et al., "Enantiomeric and Diastereoisomeric (Mixed) L/D-Octaarginine Derivatives—A Simple Way of Modulating the Properties of Cell-Penetrating Peptides", Chemistry & Biodiversity, vol. 10, 2013, pp. 1165-1184.
Sterner, et al., "Behavioral and Neurobiological Consequences of Prolonged Glucocorticoid Exposure in Rats: Relevance to Depression", Progress in Neuro-Psychopharmacology and Biological Psychiatry, vol. 34, 2010, pp. 777-790.
Wender et al., "The Design, Synthesis, and Evaluation of Molecules that Enable or Enhance Cellular Uptake: Peptoid Molecular Transporters", PNAS, vol. 97, No. 24, Nov. 21, 2000, pp. 13003-13008.
Zhao et al., "A Mouse Model of Depression Induced by Repeated Corticosterone Injections", European Journal of Pharmacology, vol. 581, 2008, pp. 113-120.

* cited by examiner

*Primary Examiner* — Sudhakar Katakam
(74) *Attorney, Agent, or Firm* — Adler Pollock & Sheehan P.C.; Michel Morency

(57) ABSTRACT

The present invention provides to compositions and methods useful in the treatment of neurological disorders including, but not limited to, Angelman syndrome, depression, traumatic brain injury, stroke, and Alzheimer's disease. CN2097, a rationally designed cyclic peptidomimetic drug that has been demonstrated to have effectiveness in preclinical models for the treatment of neurological disorders, is rapidly cleared and has a short half-life. The present invention provides a stable analog of CN2097.

1 Claim, 5 Drawing Sheets

Specification includes a Sequence Listing.

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Leu Gly Phe
1

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Arg Arg Arg Arg Arg Cys
1               5
```

```
<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(6)
<223> OTHER INFORMATION: Beta-Ala lactam side chain

<400> SEQUENCE: 3

Cys Tyr Lys Lys Thr Glu Val
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Arg Arg Arg Arg Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (6)..(8)
<223> OTHER INFORMATION: Beta-Ala lactam side chain

<400> SEQUENCE: 5

Cys Lys Asn Tyr Lys Lys Thr Glu Val
1               5
```

CYCLIC PEPTIDOMIMETIC FOR THE TREATMENT OF NEUROLOGICAL DISORDERS

CROSS-REFERENCE TO RELATED APPLICATIONS

This patent application is a continuation of U.S. patent application Ser. No. 17/036,059 filed Sep. 29, 2020 which claims priority to U.S. Provisional Patent Application No. 62/909,396 filed Oct. 2, 2019, the entire contents of which are hereby incorporated by reference herein.

FIELD OF THE INVENTION

The embodiments of the present invention relate to compositions and methods useful in the treatment of neurological disorders including, but not limited to, depression, Angelman syndrome, traumatic brain injury, stroke, and Alzheimer's disease.

SEQUENCE LISTING

The instant application contains a Sequence Listing which has been submitted electronically in ASCII format and is hereby incorporated by reference in its entirety. Said ASCII copy, created on Dec. 22, 2020, is named 405505-588001US_SL.txt and is 1,514 bytes in size.

BACKGROUND OF THE INVENTION

CN2097 (R7Cs-sCYK[KTE(β-Ala)]V) ("R7C" is disclosed as SEQ ID NO: 2 and "CYK[KTE(β-Ala)]V" is disclosed as SEQ ID NO: 3) is a rationally designed cyclic peptidomimetic that has been demonstrated to have effectiveness in preclinical models for the treatment of neurological disorders such as Angelman syndrome, traumatic brain injury (TBI), and stroke.[i] CN2097 and related compounds have been described in several patents and published patent applications.[ii] CN2097 selectively targets the PDZ binding domain of the PSD-95, a scaffolding protein involved in the development and regulation of neuronal synapses CN 2097 has demonstrated specificity for the NMDA receptor 2B (NR2B) subunit. The association of PSD-95 with NMDA receptors is an element in the propagation of the synaptic changes of LTP and long-term depression (LTD) that induce learning and memory. cPSD-95 is a member of the MAGUK-family of PDZ domain-containing proteins.

CN2097 has all the advantages of peptide-based drugs (high potency and activity, low toxicity), while small enough to remain stable and cross the blood-brain barrier (BBB). Although highly stable, the half-life of CN2097 is drastically reduced (~1 h in plasma) by the attached poly-arginine transport moiety[3] required for the transport through the blood brain barrier (BBB). Since CN2097 is cleared in a matter of hours, it's clinical potential is severely limited as it would have to be administered frequently to sustain any beneficial effects.

Because of the tremendous therapeutic potential of CN2097 for the treatment of neurological disorders, there is a need for the development of a more stable CN2097 analog with a longer circulating half-life, enabling the administration of lower doses while maintaining its therapeutic effectiveness.

BRIEF SUMMARY OF THE INVENTION

The embodiments of the present invention provide $dR_7$-2097, a more stable CN2097 analog consisting of all dextrorotary (D)-amino acids, which was shown to be more efficacious than CN2097 in animal models of neurological disorders.

In one embodiment, the present invention provides an analog of CN-2097. CN-2097 has the following structure ("$(Arg)_7$" disclosed as SEQ ID NO: 4 below):

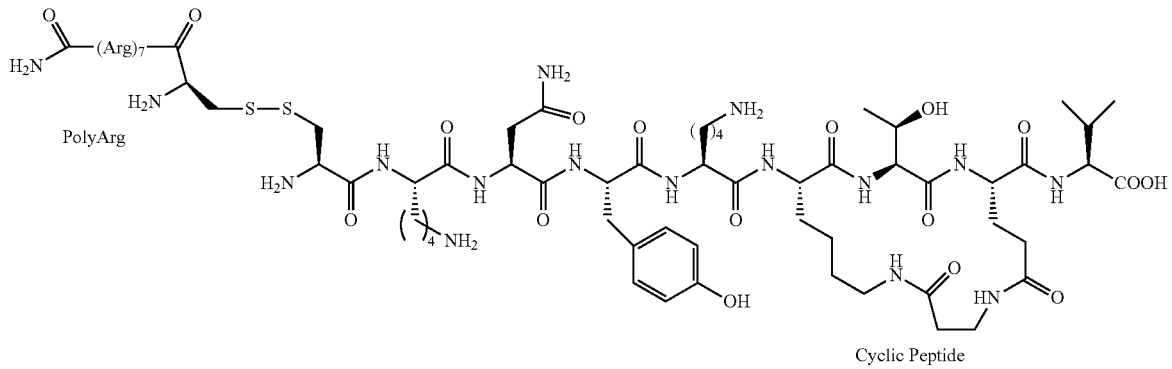

CN2097

Cyclic Peptide

The analog is represented by $dR_7$-2097 and essentially consists of dextrorotatory (D)-amino acids ($dR_7$-$NH_2$).

In another embodiment, the present invention provides a pharmaceutical composition comprising a therapeutically-effective amount of the analog of CN-2097, $dR_7$-2097, or a pharmaceutically-acceptable salt thereof, and one or more pharmaceutically-acceptable carrier.

In another aspect, the present invention provides a method of preventing or treating a neurological disorder in a subject at risk of, or afflicted with, the neurological disorder comprising administering a composition comprising (a) a therapeutically-effective amount of the analog of CN-2097, $dR_7$-2097, and (b) at least one pharmaceutically-acceptable carrier. The neurological disorders include, but are not limited to, Angelman syndrome, depression, traumatic brain injury, stroke, and Alzheimer's disease.

In one embodiment, the neurological disorder is depression. In another embodiment, the depression is treatment-resistant depression. In yet another embodiment, the depression is major depressive disorder, dysthymic disorder, psychotic depression, postpartum depression, seasonal affective disorder, bipolar disorder, bipolar depression, mood disorder, depressions caused by chronic medical conditions such as cancer or chronic pain, chemotherapy, chronic stress, post-traumatic stress disorders, or manic depressive disorder.

In yet another embodiment, the neurological disorder is Angelman syndrome, traumatic brain injury, spinal cord injury, glaucoma, stroke, cerebrovascular accident (CVA), or Alzheimer's disease.

Other implementations are also described and recited herein.

BRIEF DESCRIPTION OF THE DRAWINGS

For the purpose of illustration, certain embodiments of the present invention are shown in the drawings described below. Like numerals in the drawings indicate like elements throughout. It should be understood, however, that the invention is not limited to the precise arrangements, dimensions, and instruments shown. In the drawings:

FIG. 2A provides a schematic of the model of depression. FIG. 2B provides a bar graph showing that CN2097 decreased time spent immobile in the Tail Suspension Test (TST) but did not affect the immobility time in the Forced Swimming Test (FST). FIG. 2C shows the TST and FST one week after the CN2097 injection.

DETAILED DESCRIPTION OF THE INVENTION

Figure 1:
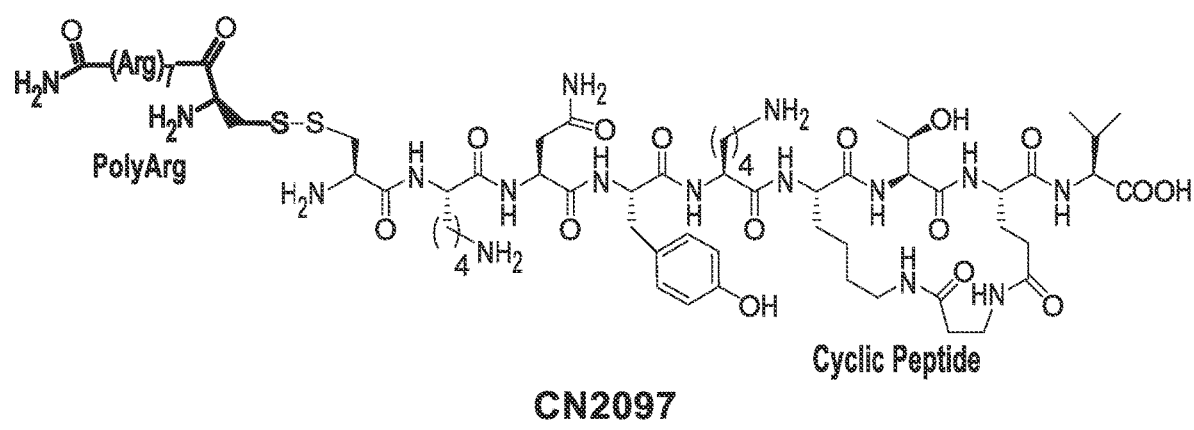
FIG. 1 shows the structure of CN2097. The PDZ-binding cyclic-ligand incorporates a unique β-alanine lactam side chain linker making this compound highly selective. Attached is a 'cell penetrating', poly-L-arginine transport moiety ($R_7$—CC-KNYK [KTE(β-Ala)]V) ("$R_7$-C" is disclosed as SEQ ID NO: 2 and "C-KNYK [KTE(β-Ala)]V" is disclosed as SEQ ID NO: 5), shown in darker black (left), which enables this compound to cross the blood brain barrier (BBB).

It is to be appreciated that certain aspects, modes, embodiments, variations and features of the invention are described below in various levels of detail in order to provide a substantial understanding of the present invention.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The term "statistically significant" or "significantly" refers to statistical significance and generally means a two standard deviation (2SD) or greater difference.

As used herein, the term "subject" refers to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human subjects. The human subject may be a pediatric, adult, or a geriatric subject. The human subject may be of either sex.

As used herein, the terms "effective amount" and "therapeutically-effective amount" include an amount sufficient to prevent or ameliorate a manifestation of disease or medical condition, such as Angelman syndrome, depression, traumatic brain injury, and Alzheimer's disease. It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a symptom or condition compared to that expected in the absence of treatment.

As used herein, the term "long-term" administration means that the therapeutic agent or drug is administered for a period of at least 12 weeks. This includes that the therapeutic agent or drug is administered such that it is effective over, or for, a period of at least 12 weeks and does not necessarily imply that the administration itself takes place for 12 weeks, e.g., if sustained release compositions or long acting therapeutic agent or drug is used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only and is not intended to limit the scope of the present invention, which is defined solely by the claims. Definitions of common terms in immunology and molecular biology can be found in THE MERCK MANUAL OF DIAGNOSIS AND THERAPY;4 THE ENCYCLOPEDIA OF MOLECULAR CELL BIOLOGY AND MOLECULAR MEDICINE;5 MOLECULAR BIOLOGY AND BIOTECHNOLOGY: A COMPREHENSIVE DESK REFERENCE;6 IMMUNOLOGY;7 JANEWAY'S IMMUNOBIOLOGY;8 LEWIN'S GENES XI;[9] MOLECULAR CLONING: A LABORATORY MANUAL;10 BASIC METHODS IN MOLECULAR BIOLOGY;11 LABORATORY METHODS IN ENZYMOLOGY; 12 CURRENT PROTOCOLS IN MOLECULAR BIOLOGY (CPMB);[13] CURRENT PROTOCOLS IN PROTEIN SCIENCE (CPPS);[14] and CURRENT PROTOCOLS IN IMMUNOLOGY (CPI).[15]

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs.

The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-micro emulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragées, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropyl methyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragées, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropyl methyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, micro-emulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically-acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art.[16]

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In other embodiments, the active compound will be administered once daily.

The patient receiving this treatment is any animal in need, including primates, in particular humans; and other mammals such as equines bovine, porcine, sheep, feline, and canine; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, l-ascorbic acid, l-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, l-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Other terms are defined herein within the description of the various aspects of the invention.

CN2097 AND dR$_7$-2097

As described above, CN2097 (R7Cs-sCYK[KTE(β-Ala)]V) ("R7C" is disclosed as SEQ ID NO: 2 and "CYK[KTE(β-Ala)]V" is disclosed as SEQ ID NO: 3) is a rationally designed peptidomimetic that has been demonstrated to have effectiveness in preclinical models for the treatment of neurological disorders such as Angelman syndrome, traumatic brain injury (TBI), and stroke. CN2097 was developed through a rational drug design approach and consists of a cyclic PDZ binding motif through a lactam ring and β-alanine linker based on last five C-terminal residues of the CRIPT scaffolding protein.[iii] Although the PDZ-binding cyclic-ligand of CN2097 is highly stable, the half-life of CN2097 is drastically reduced (~1 h in plasma) due to the attached polyarginine transport moiety required for the transport through the BBB. Since CN2097 breaks down in a matter of hours, it's clinical potential is severely limited as it would have to be administered frequently to sustain any beneficial effects.

In the present invention, a modified CN2097 analog was developed that exhibits improved affinity and specificity. An all D-polyarginine was synthesized and coupled to the cyclic PDZ-binding motif to generate dR$_7$-2097, a more stable CN2097 analog consisting solely of dextrorotary (D)-amino acids (dR$_7$—NH$_2$).

The synthesis of CN2097 has been described elsewhere.[18] The analog dR$_7$-2097 was synthesized by Peptides International. For the studies described in the Examples below, highly pure CN2097 and dR$_7$-2097 (>98% purity; 100 mg) were synthesized using our Fmoc/tBu solid phase chemistry protocol.[19]

As shown in the Examples below, dR$_7$-2097 demonstrated superior efficay compared to CN2097 in various models of neurological disorders.

Antidepressant Effects of CN2097 and dR$_7$-2097

Major Depressive Disorder (MDD) is a debilitating psychiatric disorder that affects ~7% of U.S. adults in their lifetime. MDD affects over 16 million of the U.S. population and represents a major cause of disability worldwide.[20] Drugs that increase monoaminergic signaling are the mainstay of depression therapy, however, these drugs have a delayed onset of action and are only effective in about 50% of patients.

Aberrant brain-derived neurotrophic factor (BDNF) signaling has been proposed to underlie the pathophysiology of major depressive disorder[21] and bipolar disorder.[22] Human studies and animal models support that depression is associated with reduced expression of BDNF.[23] The hippocampus is one of several limbic structures implicated in the pathophysiology of depression,[24,28,28] where BDNF and its high-affinity TrkB receptor play a critical role in synaptic plasticity.[27] Stress, a risk factor for depression, can result in hippocampal neuronal atrophy,[28] characterized by reduced synaptic connections.[29] The administration of the selective serotonin-reuptake inhibitor (SSRI) fluoxetine prevents stress-induced atrophy of dendrites and spines,[30] and reduction of TrkB receptor signaling blocks this effect.[31]

An advance in treatment was the finding that a single infusion of a sub-anesthetic dose of ketamine, an N-methyl-D-aspartate (NMDA) receptor blocker, produces rapid antidepressant effects in conventional treatment-resistant depression (TRD) patients.[32] However, ketamine's effects are temporary and limited due to cognitive side effects associated with NMDA receptor inhibition. BDNF is necessary for the rapid antidepressant effects of ketamine[33] as well as the latent response to conventional antidepressants.[34]

The discovery of rapidly acting antidepressants, such as ketamine, has transformed our ideas about depression treatment. CN2097 was developed through a rational drug design approach and consists of a cyclic PDZ binding motif through a lactam ring and β-alanine linker based on last five C-terminal residues of the CRIPT scaffolding protein.[35]

CN2097 selectively targets the PDZ binding domain of the PSD-95, a scaffolding protein involved in the development and regulation of neuronal synapses. The PDZ domain is a common structural domain of 80-90 amino-acids found in the signaling proteins of bacteria, yeast, plants, and animals. PDZ is an acronym combining the first letters of three proteins—post synaptic density protein (PSD95), Drosophila disc large tumor suppressor (DlgA), and zonula occludens-1 protein (zo-1), which were first discovered to share the domain. PDZ domains are also referred to as DHR (Dig homologous region) or GLGF (glycine-leucine-glycine-phenylalanine) (SEQ ID NO: 1) domains. These domains have been reported as helping to anchor transmembrane proteins to the cytoskeleton and hold together signaling complexes.

CN2097 has demonstrated specificity for the NMDA receptor 2B (NR2B) subunit. The association of PSD-95 with NMDA receptors is an element in the propagation of the synaptic changes of long-term potentiation (LTP) and long-term depression (LTD) that induce learning and memory. cPSD-95 is a member of the MAGUK-family of PDZ domain-containing proteins. Its basic structure includes three PDZ domains, an SH3 domain, and a guanylate kinase-like domain (GK).

A unique effect of CN2097 is that it acts downstream of TrkB to enhance long-lasting increases in synaptic strength in a BDNF-dependent manner. Our studies in Angelman mice,[36] indicate that the synaptic scaffolding protein post-synaptic density protein-95 (PSD-95) is a TrkB-associated protein essential for Akt-mTORC1 and PLC-CaMKII signaling. We previously designed a soluble cyclic-peptide drug, CN2097 (FIG. 1; MW 2376), that targets the PDZ3-domain of PSD-95 to potentiate TrkB signaling.[37] As depression is associated with memory impairment,[38] it was hypothesized that CN2097 could provide a potential new treatment for cognitive deficits.

As described in the Examples below, our preclinical studies show that CN2097 can induce rapid antidepressant effects and $dR_7$-2097 demonstrated superior efficay compared to CN2097.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. Although methods and materials similar or equivalent to those described herein can be used in the practice or testing of this disclosure, suitable methods and materials are described below.

EXAMPLES

The invention now being generally described, it will be more readily understood by reference to the following examples which are included merely for purposes of illustration of certain aspects and embodiments of the present invention and are not intended to limit the invention.

Example 1 Antidepressant Effects of CN2097

Depressive symptomatology has been reliably characterized using exogenous corticosterone (CORT) administration, e.g., dendritic atrophy in hippocampal pyramidal cells with loss of CA3 and CA1 apical dendrites.[39] Importantly, CORT administration leads to impaired BDNF-mediated signaling and synaptic plasticity in limbic and forebrain regions. In this model, ketamine, which is known to be effective for the treatment of TRD, significantly reduced depressive-like behavior.[40]

We hypothesize that antidepressant-like effects of ketamine and CN2097 are mediated via the same signaling pathways, e.g., by the activation of mTOR. The effects of i.v. CN2097 on the depressive-like behavior of repeated corticosterone-injected mice were examined in the Chronic mild stress (CMS) animal model, which comprise both physical and social stressors.[41]

Figure 2A:
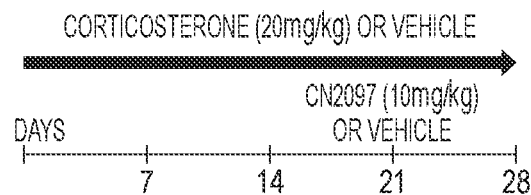
FIG. 2A-C shows that CN2097 reverses depression-like behavior in mice.

Mice were divided into two groups, namely, control (Ctrl) and CORT. The mice in the CORT group were injected with CORT (i.p., 20 mg/kg), once per day at random times during the light phase. Control mice were injected with the vehicle.[42] A schematic of the model of depression is illustrated in FIG. 2A.

Figure 2B:
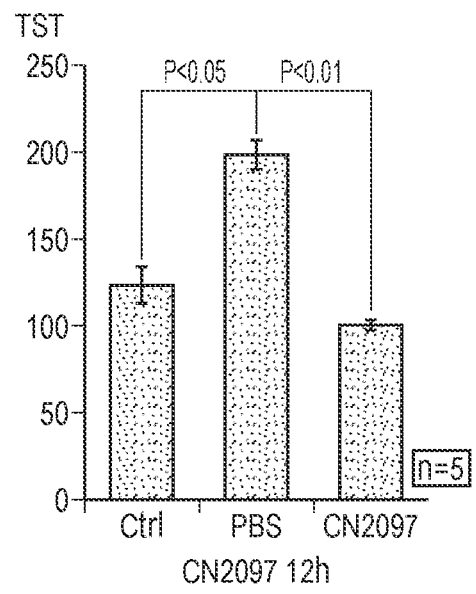
Figure 2C:
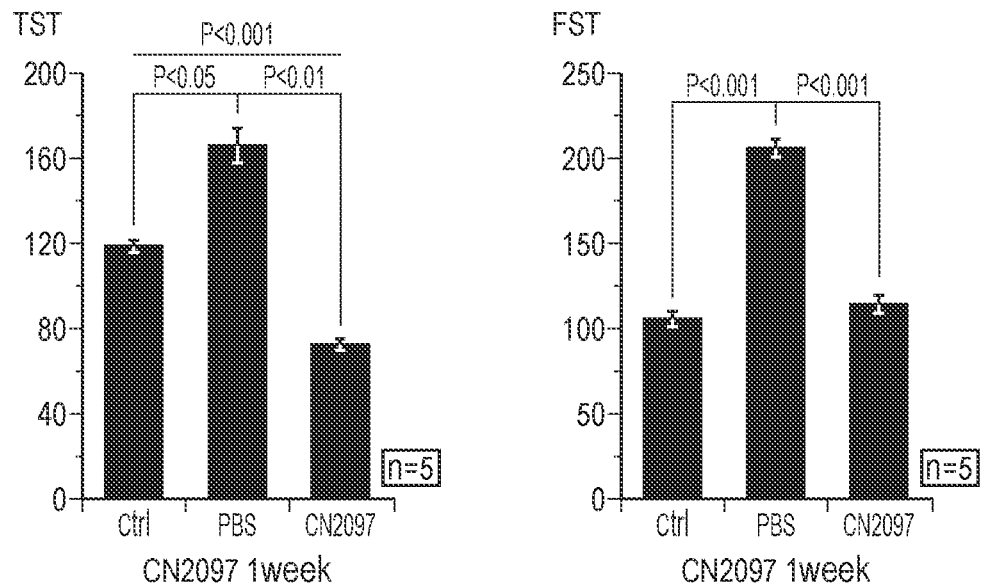

As illustrated in FIG. 2, CN2097 reversed depression-like behavior in mice; CN2097 significantly decreased time spent immobile in both the TST and the FST. CN2097 (tail vein injection, 12 hours before TST onset) significantly decreased the time spent immobile in the TST (FIG. 2B) but did not affect the immobility time in the FST (data not shown). CN2097 (tail vein injection, 1 week before TST onset) significantly decreased the time spent immobile in both the TST and the FST (FIG. 2C).

Figure 3:
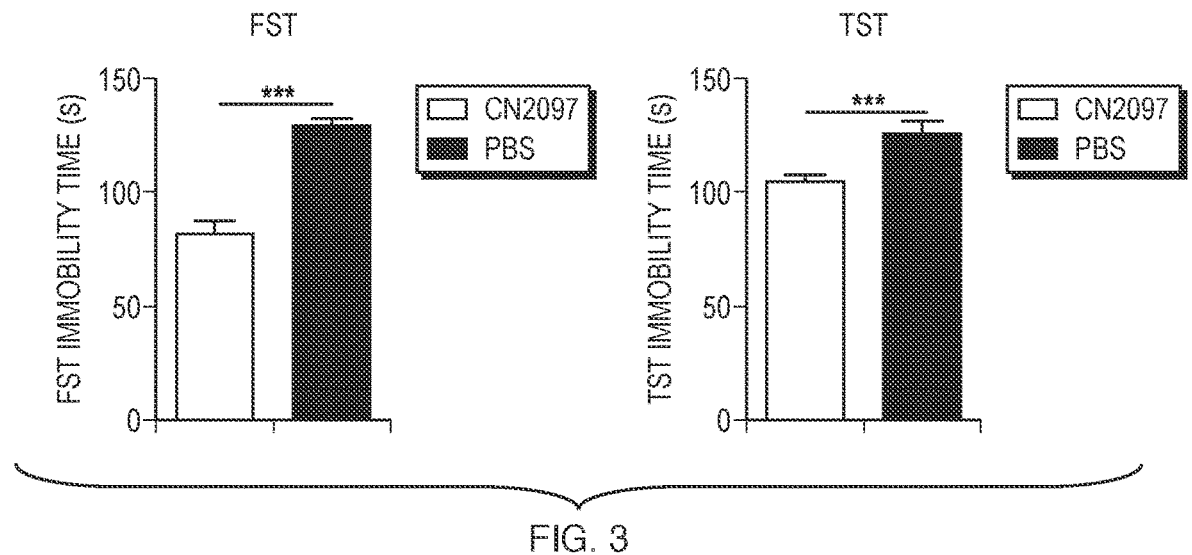
FIG. 3 shows that CN2097 mitigates the effects of Chronic Mild Stress (CMS) on the Elevated Plus Maze (EPM, left panel) and the Novelty-Suppressed Feeding (NSF, right panel). Data are means±SEMs (n=10/group). ***$p<0.001$ compared to control (two-way ANOVA, Bonferroni post-test).

As shown in FIG. 3, a single injection of CN2097 also exhibited anti-depressant efficacy in the CMS model within 2 hours, suggesting a rapid antidepressant response. Day 7 after injection of CN2097, immobility times in the FST and TST were tested as described in Marshall (2018).[43] The acute injection of CN2097 significantly reduced the duration of immobility time in both the Forced Swim Test (FIG. 3, left panel) and the Tail Suspension Test (FIG. 3, right panel).

As described above, aberrant brain-derived neurotrophic factor (BDNF) signaling has been proposed to underlie the pathophysiology of major depressive disorder and bipolar disorder. An advance in treatment was the finding that a single infusion of a sub-anesthetic dose of ketamine, an NMDA receptor blocker, produces rapid antidepressant effects in conventional treatment-resistant depression (TRD) patients. However, ketamine's effects are temporary and limited due to cognitive side effects associated with NMDA receptor inhibition. BDNF is necessary for the rapid antidepressant effects of ketamine as well as the latent response to conventional antidepressants. With over 5 million people in the U.S. suffering from treatment-resistant depression, there is an urgent need for the development of new antidepressant drugs. CN2097 has been shown to potentiate BDNF signaling pathways.

In the present Example 1, CN2097 was shown to produce rapid antidepressant effects in a chronic mild stress (CMS) mouse model, suggesting that this cyclic peptidomimetic compound is a potential therapeutic for TRD.

Example 2 CN2097 Reverses Behavioral Alterations Induced in the CMS Model

To further test CN2097, we used the Chronic Mild Stress (CMS) model which has been shown to evoke anxiety and lower sucrose consumption (postulated to reflect anhedonia), symptoms associated with MDD. As described in Marshall (2018),[44] mice subjected to repeated daily stress for 3 weeks, then received a single injection of CN2097 (10 mg/kg) or vehicle.

Figure 4:
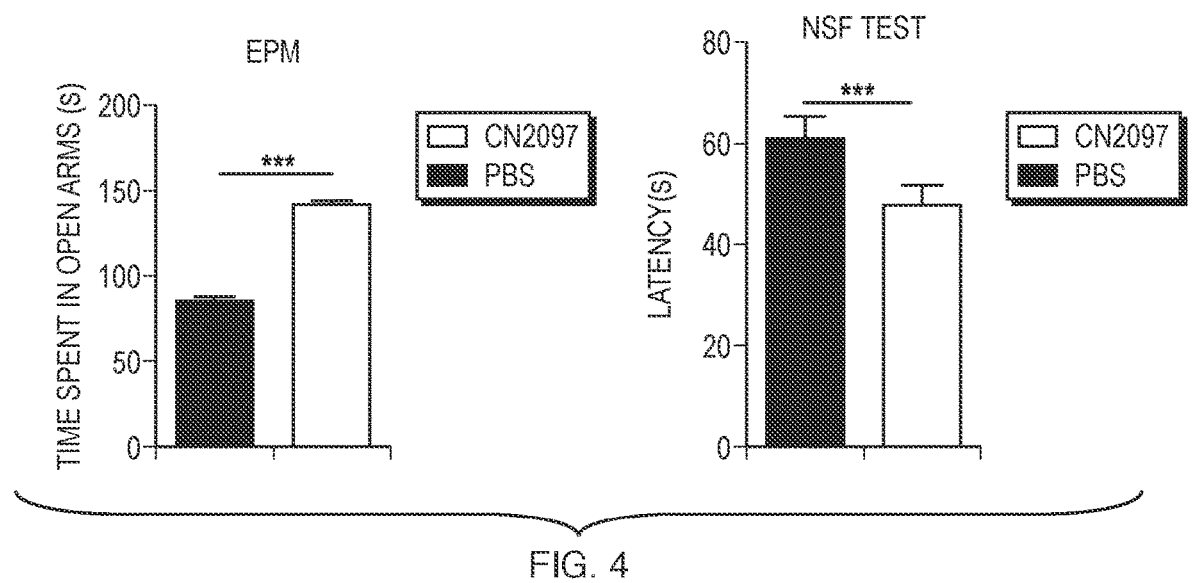
FIG. 4 shows that acute injection of CN2097 reduced the duration of immobility time in both the Forced Swim Test (FST, left panel) and the Tail Suspension Test (TST, right panel). ***$p<0.001$ vs. control mice.

The acute effects of CN2097 on anxiety were evaluated by the elevated plus-maze (EPM) and novelty-suppressed feeding (NSF) tests. As shown in FIG. 4 (left panel), CN2097 increased the time spent in open arms in the EPM.

In the NSF test, anxiety-induced hypophagia was assessed by measuring the latency of mice to eat a familiar food in an aversive environment. As shown in FIG. 4 (right panel), the administration of CN2097 1 hour prior to testing significantly shortened the latency period until feeding. These data suggest that CN2097 effectively reverses behavioral alterations induced in the CMS Model.

The CMS model responds to chronic, but not acute, administration of established antidepressant drugs.[45] Based on the predictive value of the CMS model,[46] the above-described data showing that CN2097 caused a reversal of anhedonic and other behavioral effects within 2 hours (FIGS. 3-4) suggests that it provides rapid ketamine-like antidepressant actions.

Example 3 Antidepressant Effects of CN2097 and dR$_7$-2097

The discovery of rapidly acting antidepressants, such as ketamine, has transformed our ideas about depression treatment. Based on the above-described data (FIGS. 2-4), CN2097 elicits rapid antidepressant effects that merits further testing. Moreover, although dR$_7$-2097 is a stable analog that is not cleared rapidly like CN2097, its functional efficacy remains to be determined and compared to CN2097 in an animal model of depression. Accordingly, the effects of CN2097 and dR$_7$-2097 on memory recall were assessed in the Contextual Fear Conditioning (CFC) test.[47]

Mice received i.p. injections of 1, 5, or 10 mg/kg CN2097 or 1 or 5 mg/kg dR$_7$-2097.

Figure 5:
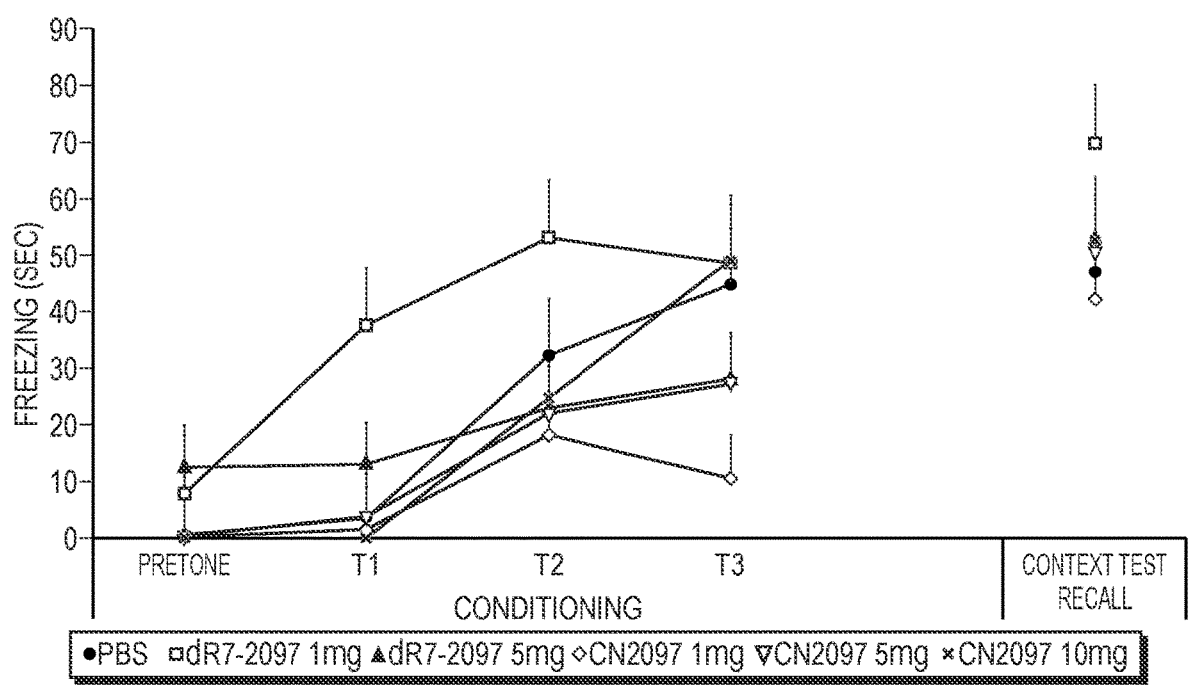
FIG. 5 shows that $dR_7$-2097 significantly increasing recall in the contextual fear conditioning (CFC) test and was more efficacious than CN2097.

As shown in the FIG. 5, dR$_7$-2097 was more efficacious than CN2097 in significantly increasing memory recall in the CFC test. These results show that it is possible to modify CN2097 with (D)-amino acids and not only maintain the efficacy but enhance it. The suggests that the increased stability will enable the administration of lower doses (10 fold or more) while maintaining anti-depressive properties.

Example 4 Effects of CN2097 and dR$_7$-2097 in an Angelman Syndrome Mouse Model

The functional efficacy of dR$_7$-2097 was also assessed and compared to CN2097 in an animal model of Angelman Syndrome (AS).

Disruptions in long-term potentiation (LTP) lead to disruptions in memory and has been associated with several neurological disorders, including autism syndromes and neurodegenerative disorders. LTP failure is also implicated in AS. It is believed that AS is a neurogenetic disorder characterized by intellectual and developmental delay, sleep disturbance, seizures, jerky movements especially hand-flapping, frequent laughter or smiling, and usually a happy demeanor. Some believe that AS is a classic example of genetic imprinting in that it is usually caused by deletion or inactivation of genes on the maternally inherited chromosome 15. The related syndrome, Prader-Willi syndrome, is believed caused by a similar loss of paternally-inherited genes.

AS is a result of loss-of-function mutations or deletions in the maternally inherited allele of UBE3A. Mice that are deficient in maternal Ube3a also show genetically reversible deficits in learning and the induction of hippocampal (LTP),[48,49,50] a form of synaptic plasticity. Angelman syndrome (AS) is caused by disruptions in function due to mutations and/or deletions in the maternally inherited allele of an E3 ubiquitin ligase, UBE3A, a gene that has also been implicated in the broader spectrum of Autism patients.

A mouse model for AS carries the maternally inherited Ube3a-null mutation and shows profound impairments in hippocampal synaptic plasticity.[51] It has been reported that UBE3A is also required for experience dependent maturation in the visual cortex. In particular, AS mice show deficits in long-term potentiation (LTP) and long-term depression (LTD), which are the cellular substrates of learning and memory. These forms of synaptic plasticity are highly regulated by activity-dependent changes in the ratio of NMDA subunits, specifically NR2A and NR2B subunits. NMDA receptors gate the influx of calcium ions across the post-synaptic membrane. Depending on the characteristics of the calcium influx generated in response to pre-synaptic activity, either LTP or LTD can be induced. This calcium influx activates calcium-dependent enzymes such as CaMKII, which has been strongly implicated in AS, and triggers its autophosphorylation at Thr286. This autophosphorylation is very important as it allows the enzyme to remain active once the calcium levels return to normal. This pathway requires an interplay between the NMDA receptor, CaMKII and a post-synaptic scaffolding protein (PSD-95 in particular), which brings these biochemical elements into proximity. Thr286 autophosphorylation is instrumental in promoting the association of CaMKII with the PSD by directly binding to the NMDA receptor. Interestingly, there is also a secondary inhibitory autophosphorylation at Thr305/306 that has been suggested to regulate the association of CaMKII to the PSD. Interplay between these states can govern the availability of CaMKII to regulate synaptic plasticity in response to calcium influx during learning and memory activity. The clinical features of AS have been linked to the misregulation of alpha CaMKII function. The role of CaMKII in synaptic plasticity and AS has been investigated at the synapses of the Schaffer-collateral-CA1 pyramidal cells in the adult hippocampus.

CN2097 has previously been shown to restore hippocampal LTP in an Angelman Syndrome mouse model.[52] After in vivo administration of CN2097, the mouse was sacrificed and CA1 hippocampal LTP measured by extracellular field potential recordings, and the level of potentiation compared to control C57BL/6 mice, which robustly generate long-lasting LTP. In the present study, we tested whether in vivo administration dR$_7$-2097 would reverse the well-established LTP impairment observed in the hippocampus of AS mice.

Figure 6:
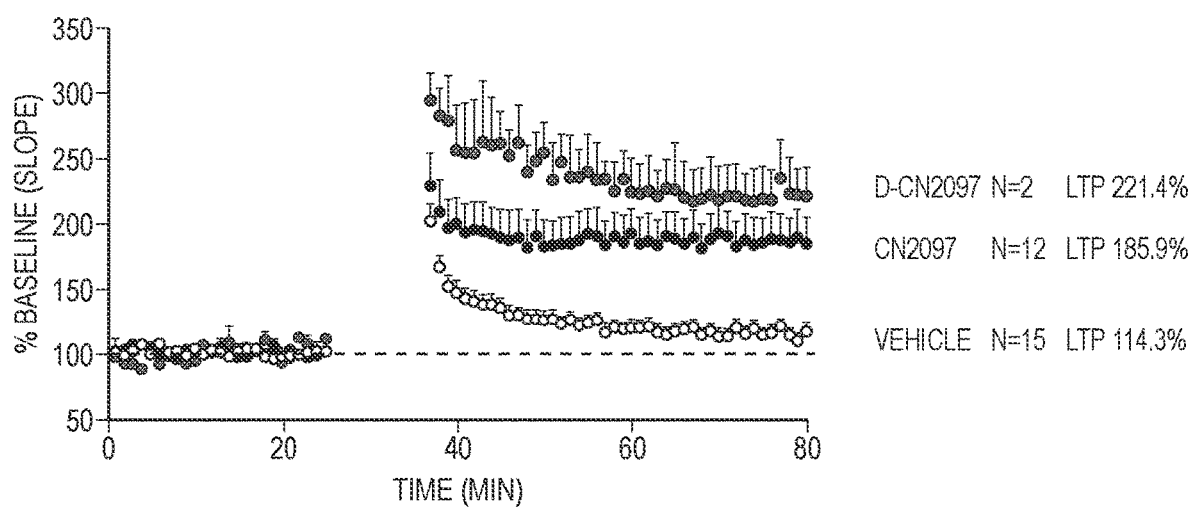
FIG. 6 provides a line graph showing that $dR_7$-2097 (D-CN2097) is more efficacious than CN2097 in restoring hippocampal long term potentiation (LTP) in an Angelman Syndrome mouse model.

Typically, 10 mg/kg of CN2097 needs to be injected into AS mice and use of a severe 3×HFS protocol in order to reinstate LTP in AS hippocampal brain slices. With dR$_7$-2097, a lower dose (2.5 mg/kg) and a modest LTP-inducing stimulus of 2×HFS protocol was sufficient to significantly increased the LTP induction rate in AS hippocampal slices prepared 2 hours after dR$_7$-2097 injection. LTP was observed in 67% of AS slices recorded with a mean fEPSP slope of 221 (n=2 of 3). As shown in FIG. 6, dR$_7$-2097 was more efficacious than CN2097 in restoring hippocampal LTP in the AS mouse model.

Example 5 Treatment of Neural Injuries

A stroke, or cerebrovascular accident (CVA), is the rapid loss of brain function due to disturbance in the blood supply to the brain. This can be due to ischemia (lack of blood flow) caused by blockage (thrombosis, arterial embolism), or a hemorrhage (broadly termed "neurological insult"). As a result, and often worsening over time, brain injury becomes permanent dysfunction/damage. Typically, affected areas of the brain have diminished or complete loss of function. In particular instances this is exhibited as an inability or reduced ability to move one or more limbs on one side of the body, inability to or difficulty in understanding or formulating speech, or an inability to see one side of the visual field. In the case of stroke, secondary neuronal damage following the initial insult is a significant factor in patient decline and eventual death. This decline manifests itself weeks to months following the initial stoke and, without effective therapeutic intervention, leads to a slow but continuous decline in the patients physical and mental health.

In the case of TBI, the progression of damage is typically slower than that in stroke. Recent reports, however, establish TBI as equally destructive in outcome in the more severe cases. Current reports find that about 40% of people with TBI exhibit a continuing decline in both physical and mental capacity. This represents a significantly higher incidence of dementia, in some instances is an aggravating factor in death.

An important consideration in therapeutic treatment and improved outcomes in patients afflicted with neuronal injury (including either Stroke or TBI) is to block secondary injury of surrounding neurons that were not, in the first instance, directly affected by the primary insult. Literature reports that secondary neuronal damage occurs after a variety of brain insults including subarachnoid hemorrhage, stroke, and traumatic brain injury and involves metabolic cascades. Noted metabolic aspects include prolonged secondary ischemia, cerebral hypoxia, hypotension, cerebral edema, changes in the blood flow to the brain; and raised intracranial pressure. Other secondary insults include hypercapnia, acidosis, meningitis, and brain abscess. In addition, alterations in the release of neurotransmitters particularly glutamate can cause excitotoxic neuronal cell death by causing free radicals generation and oxidative stress within these neurons that leads to neurodegeneration.

CN2097 and dR7-2097 are both capable of neuroprotection. Without being bound by any particular theory, reference is made to the strong positive charge of the polyarginine compositions, e.g., over all charge of the peptide is +7 with 7 arginine residues (SEQ ID NO: 4). Notably, substituting lysine (also positively charged) for arginine in the presence or absence of a terminal cysteine did not provide neuroprotection. Further, a peptide with at least 5 or more arginine residues can be flanked by 1 or 2 neutral amino acids and still be therapeutically active.

Because it is cleared less rapidly, $dR_7$-2097 is more effective than CN2097 for neuroprotection. Reference is made to the chiral nature of arginine and cysteine, e.g., d-based compositions (e.g., d-R) had superior neuroprotective properties. The terminal cysteine(s) are contemplated as attached at either/both the N-terminus or C-terminus via peptide bond and to reduce the reactivity of the exposed SH group, will have the option of being protected by way of a disulfide linkage to a second cysteine (designated here as C-s-s-C).

Dosing is stated for $dR_7$-2097 compositions but is similar for all compositions disclosed herein. Broadly, therapeutically effective dosages intraventricular or intrathecal administrations range from about 1,000 μg/kg to about 1 μg/kg. For i.v administrations, therapeutically effective dosages from about 0.01 mg/kg to about 20 mg/kg. All forms of administration are contemplated. Dosing should be instituted is soon as possible after the subject presents with a neuronal injury, e.g., stroke-like indicia or traumatic brain injury.

In a test model, the retina was protected from NMDA-induced chemical stroke. Notably d-amino acid peptides are resistant to most protease digestion and, in some embodiments, exhibit longer half-life in vivo. The compositions of this invention are useful in a variety of clinical situations, most of which are characterized by neurological insult or cellular insult typified by mitochondrial damage. Without being bound by any particular theory, untreated mitochondrial damage is believed to lead to generation of free radical species. The compositions of this invention appear to avert or curtail oxidative stress in the retina following NMDA-insult by reducing mitochondrial originated free radical generation. Without being bound by any particular theory, such activity is believed to be significant in neuroprotection arising from the compositions of this invention.

Particular reference is made to neuronal injuries such as stroke and TBIs (including closed head injuries, e.g., sports-related injuries, accidental injuries involving a concussion, blast injuries (combat or other). In one embodiment, football players and boxers are dosed prophylactically prior to a game, practice, or bout. Additionally, dosing may be immediately after first contact in a scheduled game or bout. Dosing is based on an assumption of neurological insult or incipient damage without regard to actual (detected) presenting symptoms.

Prophetic Examples

Stroke Patient

A 57 year old male enters the emergency room and is diagnosed with an ischemic event involving the middle cerebral artery, with symptomatology onset being under 1 hour. Immediately, the patient was administered an i.v. supplemented with $dR_7$-2097 while blood supply to the restricted area is restored.

Daily testing of cognitive and motor systems show no deficits in physical or mental capacities. In addition, CT/MRI imaging show no signs of lesioning in the affected region, immediately following recovery and that this was maintained and confirmed by follow-up imaging and behavior testing.

Post-Stroke Patient

A 64 year old woman is revived following stoke in her home by EMS and is rushed to the nearest hospital 80 miles away. Upon arriving at the hospital, it is determined that the patient is showing signs of weakness on her left side. In addition, she complains of having blurred vision and exhibits difficulty in speaking clearly. She is immediately started an i.v. and administered $dR_7$-2097 (4 mg/kg/hr over a period of 5 days) to arrest post-stroke neuronal damage.

The patient is monitored for recovery signs. Improvement in her speech pattern is noted over the next 30 days as is increased muscle tone on the left side and muscle recovery strength and usage of her effected limbs.

TBI Patient

A 17 year old high school football player is rushed to the emergency room of a local hospital suffering from a severe concussion following a helmet to helmet impact with an opposing player. The patient is initially unconscious on the field for over 20 min. EMS personnel arrived to find the patient responding to stimuli, but completely disoriented and unable to coordinate muscle movement, articulate speech or focus eye movements.

Upon arriving at the ER, the patient is administered an i.v. containing $dR_7$-2097 at 0.05 mg/kg. Delivery is continued until brain swelling resulting from the impact returns to normal state (3-5 days). Without being bound by any particular theory, the therapeutic is to arrest neuronal cell death resulting from these documented post-traumatic effects.

Monitoring the patient though this period (and beyond) shows that he remains symptom free of TBI and post-concussion effects (i.e., avoiding short-term memory loss or exhibiting longer-term learning deficits).

TBI Patient

The same scenario as above is noted here, except the $dR_7$-2097 dosage is 20 mg/kg.

Spinal Cord Injury

A 30 year old female presents with a spinal cord injury following an automobile accident. The subject is conscious but unable to move her legs. Multi-slice spiral computed tomography (MSCT) demonstrates a foreign body in spinal canal at the level of the Th11-Th12. A Th(11)-L(2) laminectomy is performed along with retrieval of foreign bodies and dura repair. Upon admission, the patient is administered an i.v. containing $dR_7$-2097 at 0.15 mg/kg. Delivery of the peptide is continued every other day for 30 days when substantial ability to move her legs is returned.

Glaucoma

A 60 year old female presents with a complaint of blurry vision in her left eye for 1 week. Her intraocular pressure (10P) is above 21 mmHg. A diagnosis of glaucoma is made.

Effort is made to surgically reduce the IOP. In post-surgical monitoring, 10P levels remain above normal accepted levels. To prevent retinal damage resulting from the prolonged exposure to elevated 10P, the patient is administered $dR_7$-2097 in the form of eye drops suspended in a corneal penetrating lipophilic suspension. Each 20 µL drop contains 1.25 µg of $dR_7$-2097. The total applied/treatment is 2.5 µg $dR_7$-2097; two drops are administered morning and two drops at night.

Treatment is continued chronically, and no progression of neuronal cell death is detected.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize or be able to ascertain using no more than routine experimentation, many equivalents to the specific embodiments described herein. Such equivalents are intended to be encompassed by the following claims.

REFERENCES

[3] Purkayastha, N. (2013). Enantiomeric and Diastereoisomeric (Mixed) *L/D-Octaarginine Derivatives—A Simple Way of Modulating the Properties of Cell-Penetrating Peptides.* Chemistry & Biodiversity 10(7):1165-1184.

[4] THE MERCK MANUAL OF DIAGNOSIS AND THERAPY, 19th Edition, published by Merck Sharp & Dohme Corp., 2011 (ISBN 978-0-911910-19-3).

[5] THE ENCYCLOPEDIA OF MOLECULAR CELL BIOLOGY AND MOLECULAR MEDICINE, Robert S. Porter et al. (eds.), published by Blackwell Science Ltd., 1999-2012 (ISBN 9783527600908).

[6] MOLECULAR BIOLOGY AND BIOTECHNOLOGY: A COMPREHENSIVE DESK REFERENCE, Robert A. Meyers (ed.), published by VCH Publishers, Inc., 1995 (ISBN 1-56081-569-8).

[7] IMMUNOLOGY, Werner Luttmann (ed.), published by Elsevier, 2006.

[8] JANEWAY'S IMMUNOBIOLOGY, Kenneth Murphy, Allan Mowat, Casey Weaver (eds.), Taylor & Francis Limited, 2014 (ISBN 0815345305, 9780815345305).

[9] LEWIN'S GENES XI, published by Jones & Bartlett Publishers, 2014 (ISBN-1449659055).

[10] MOLECULAR CLONING: A LABORATORY MANUAL, 4th ed., Michael Richard Green and Joseph Sambrook (eds.), Cold Spring Harbor Laboratory Press, Cold Spring Harbor, N.Y., USA (2012) (ISBN 1936113414).

[11] BASIC METHODS IN MOLECULAR BIOLOGY, Davis et al. (eds.), Elsevier Science Publishing, Inc., New York, USA (2012) (ISBN 044460149X).

[12] LABORATORY METHODS IN ENZYMOLOGY: DNA, Jon Lorsch (ed.) Elsevier, 2013 (ISBN 0124199542).

[13] CURRENT PROTOCOLS IN MOLECULAR BIOLOGY (CPMB), Frederick M. Ausubel (ed.), John Wiley and Sons, 2014 (ISBN 047150338X, 9780471503385).

[14] CURRENT PROTOCOLS IN PROTEIN SCIENCE (CPPS), John E. Coligan (ed.), John Wiley and Sons, Inc., 2005.

[15] CURRENT PROTOCOLS IN IMMUNOLOGY (CPI), John E. Coligan, ADA M Kruisbeek, David H Margulies, Ethan M Shevach, Warren Strobe, (eds.) John Wiley and Sons, Inc., 2003 (ISBN 0471142735, 9780471142737).

[16] See, e.g., HARRISON'S PRINCIPLES OF INTERNAL MEDICINE, 13 ed., Isselbacher, et al. (eds.), (1996). 1814-1882.

[18] See, e.g., US Published Application Nos. 2015/0038671, 20160303186, 20120220535; U.S. Pat. Nos. 10,046,024, 9,403,876.

[19] Darwish S., et al. (2017). *Efficient synthesis of CN2097 using in situ activation of sulfhydryl group.* Tetrahedron Lett. 2; 58(31): 3053-3056.

[20] Kessler, R. C. and Bromet, E. J. (2013). *The epidemiology of depression across cultures.* Annu. Rev. Public Health 34: 119-138.

[21] Phillips, C. (2017). *Brain-Derived Neurotrophic Factor, Depression, and Physical Activity: Making the Neuroplastic Connection.* Neural Plast. 2017: 7260130.

[22] Scola, G. and Andreazza, A. C. (2015). *The role of neurotrophins in bipolar disorder.* Prog. in Neuro-Psychopharm. & Biol. Psych. 56: 122-128.

[23] Arumugam, V. et al. (2017). *The impact of antidepressant treatment on brain-derived neurotrophic factor level: An evidence-based approach through systematic review and meta-analysis.* Indian J. Pharmacol. 49(3): 236-242.

[24] Björkholm, C. and Monteggia L. M. (2016). *BDNF—a key transducer of antidepressant effects.* Neuropharmacology 102: 72-79.

[25] Marsden, W. N. (2013). *Synaptic plasticity in depression: molecular, cellular and functional correlates.* Prog. Neuropsychopharmacol. & Biol. Psych. 43:168-184.

[26] Castrén E. and Rantamäki, T. (2010). *The role of BDNF and its receptors in depression and antidepressant drug action: Reactivation of developmental plasticity.* Dev. Neurobiol. 70(5): 289-297.

[27] Minichiello, L. (2009). *TrkB signalling pathways in LTP and learning.* Nat. Rev. Neurosci. 10(12): 850-860.

[28] Watanabe, Y. et al. (1992). *Stress induces atrophy of apical dendrites of hippocampal CA3 pyramidal neurons.* Brain Res. 588(2): 341-345.

[29] Wohleb, E. S., et al. (2018). *Stress-Induced Neuronal Colony Stimulating Factor 1 Provokes Microglia-Mediated Neuronal Remodeling and Depressive-like Behavior.* Biol. Psychiatry 83(1): 38-49.

[30] Bessa J. M., et al. (2009). *The mood-improving actions of antidepressants do not depend on neurogenesis but are associated with neuronal remodeling.* Mol. Psychiatry 14: 764-773.

[31] Chen Z Y, et al. (2006). *Genetic variant BDNF (Val66Met) polymorphism alters anxiety-related behavior.* Science 314:140-143.

[32] Serafini, G., et al. (2014). *The Role of Ketamine in Treatment-Resistant Depression: A Systematic Review.* Curr. Neuropharmacol. 12(5): 444-461.
[33] Wohleb, E. S., et al. (2017). *Molecular and Cellular Mechanisms of Rapid-Acting Antidepressants Ketamine and Scopolamine.* Curr. Neuropharmacol. 15(1): 11-20.
[34] Nibuya, M., et al. (1995). *Regulation of BDNF and trkB mRNA in rat brain by chronic electroconvulsive seizure and antidepressant drug treatments.* J. Neurosci. 15: 7539-7547.
[35] Piserchio, A., et al. (2004). *Targeting specific PDZ domains of PSD-95; structural basis for enhanced affinity and enzymatic stability of a cyclic peptide.* Chem Biol. 11(4): 469-473.
[36] Cao, C. et al. (2013). *Impairment of TrkB-PSD-95 signaling in Angelman syndrome.* PLoS Biol. 11(2): e1001478.
[37] Piserchio A., et al. (2004). *Targeting specific PDZ domains of PSD-95; structural basis for enhanced affinity and enzymatic stability of a cyclic peptide.* Chem. Biol. 11(4): 469-473.
[38] Hammar, Å. and Årdal, G. (2009). *Cognitive Functioning in Major Depression—A Summary.* Front Hum. Neurosci. 3: 26.
[39] Sterner, E. Y. and Kalynchuk, L. E. (2010). *Behavioral and neurobiological consequences of prolonged glucocorticoid exposure in rats: relevance to depression.* Prog. Neuropsychopharmacol. & Biol. Psych. 34: 777-790.
[40] Koike, H., et al. (2013). *Effects of ketamine and LY341495 on the depressive-like behavior of repeated corticosterone-injected rats.* Pharmacol. Biochem. Behav. 107: 20-23.
[41] Willner, P. (2017). *The chronic mild stress (CMS) model of depression: History, evaluation and usage.* Neurobiol. Stress 6: 78-93.
[42] See, Zhao, Y., et al. (2008). *A mouse model of depression induced by repeated corticosterone injections.* Eur. J. Pharmacol. 581(1-2): 113-120.
[43] Marshall J., et al. (2018). *Antidepression action of BDNF requires and is mimicked by Gαi1/3 expression in the hippocampus.* PNAS 115 (15): E3549-E3558.
[44] Marshall J., et al. (2018). *Antidepression action of BDNF requires and is mimicked by Gαi1/3 expression in the hippocampus.* PNAS 115 (15): E3549-E3558.
[45] Willner, P. (2017). *The chronic mild stress (CMS) model of depression: History, evaluation and usage.* Neurobiol. Stress 6: 78-93.
[46] Abelaira, H. M., et al. (2013). *Animal models as tools to study the pathophysiology of depression.* Braz. J. Psychiatr. 35 Suppl 2: S112-120.
[47] van Boxelaere, M., et al. (2017). *Unpredictable chronic mild stress differentially impairs social and contextual discrimination learning in two inbred mouse strains.* PLoS One 12, e0188537.
[48] Jiang, Y.-h., et al. (1998). *Mutation of the Angelman Ubiquitin Ligase in Mice Causes Increased Cytoplasmic p53 and Deficits of Contextual Learning and Long-Term Potentiation.* Neuron 21, 799-811.
[49] Weeber, E. J., et al. (2003). *Derangements of Hippocampal Calcium/Calmodulin-Dependent Protein Kinase II in a Mouse Model for Angelman Mental Retardation Syndrome.* J. Neurosci. 23, 2634-2644.
[50] van Woerden, G. M., et al. (2007). *Rescue of neurological deficits in a mouse model for Angelman syndrome by reduction of αCaMKII inhibitory phosphorylation.* Nat. Neurosci. 10, 280-282.
[51] U.S. Pat. No. 8,673,857.
[52] See, e.g., U.S. Pat. No. 8,673,857.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of treating a neurological disorder in a subject afflicted with the neurological disorder comprising administering a composition comprising (a) a therapeutically-effective amount of dR$_7$-2097 and (b) at least one pharmaceutically-acceptable carrier, wherein the dR$_7$-2097 comprises RRRRRRRC (SEQ ID NO: 2 or PolyArg) in the following dR$_7$-2097 structure:

dR$_7$-2097

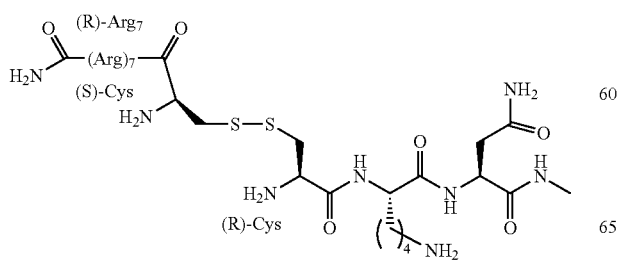

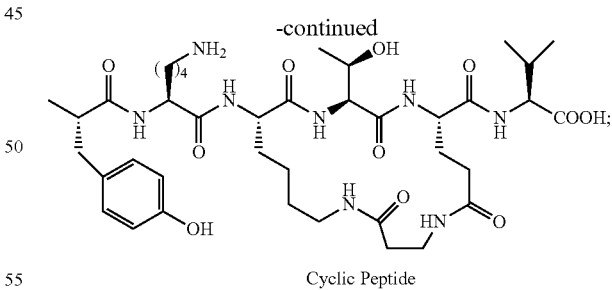

Cyclic Peptide wherein the PolyArg consists of all the R enantiomer, (R)-Arg or ("R")-arginine, and all the S enantiomer, ("S")-cysteine amino acids in the RRRRRRRC (SEQ ID NO: 2);

wherein in dR$_7$-2097 there is a disulfide linkage from the (S)-Cys or ("S")-cysteine to one (R)-Cys or ("R")-cysteine;

wherein the PolyArg is operative to transport the dR$_7$-2097 across the blood-brain barrier (BBB) in the subject, and the dR$_7$-2097 is at least four times more efficacious than CN2097 in treating the neurological disorder; and wherein the neurogical disorder is major depressive disorder.

\* \* \* \* \*